United States Patent [19]

Siegel et al.

[11] Patent Number: 5,217,698

[45] Date of Patent: Jun. 8, 1993

[54] OFFICE SIZE INSTRUMENT STERILIZATION SYSTEM

[75] Inventors: Norman L. Siegel, Mentor; David E. Minerovic, Concord; Raymond C. Kralovic, Austinburg; Bill R. Sanford, Mentor; Pamela C. Tanner, Euclid; Donald J. Rebele; Douglas F. Marshall, both of Worthington; Samuel M. Fung, Columbus, all of Ohio; John L. Beiswenger, Coatesville, Pa.

[73] Assignee: Steris Corporation, Mentor, Ohio

[21] Appl. No.: 681,118

[22] Filed: Apr. 5, 1991

Related U.S. Application Data

[63] Continuation-in-part of Ser. No. 349,304, May 9, 1989, Pat. No. 5,091,343, and a continuation-in-part of Ser. No. 342,189, Apr. 24, 1989, Pat. No. 5,116,575, said Ser. No. 349,304, May 5, 1989 Pat. No. 5,091,343, is a continuation-in-part of Ser. No. 140,388, Jan. 4, 1988, Pat. No. 4,892,706, said Ser. No. 342,189, April 24, 1989, Pat. No. 5,116,575, is a continuation-in-part of Ser. No. 229,917, Aug. 8, 1988, Pat. No. 5,077,008, which is a continuation-in-part of Ser. No. 140,388, Jan. 4, 1988, Pat. No. 4,892,706, and a continuation-in-part of Ser. No. 165,189, Mar. 7, 1988, Pat. No. 5,037,623, said Ser. No. 140,388, Jan. 4, 1988, Pat. No. 4,892,706, is a continuation-in-part of Ser. No. 826,730, Feb. 6, 1986, Pat. No. 4,731,222, said Ser. No. 165,189, Mar. 7, 1988, Pat. No. 5,037,623, is a continuation-in-part of Ser. No. 826,730, Feb. 6, 1986, Pat. No. 4,731,222.

[51] Int. Cl.[5] .................. A61L 2/18; B08B 13/00
[52] U.S. Cl. .................. 422/295; 134/94.1; 134/100.1; 422/292; 422/297; 422/300
[58] Field of Search .......... 422/292, 295, 297, 300; 277/168; 134/60, 94, 100

[56] References Cited

U.S. PATENT DOCUMENTS 4,795,173 1/1989 Osborne .................. 277/168
4,959,199 9/1990 Brewer .................. 422/300
5,091,343 2/1992 Schneider et al. .................. 422/292 X Primary Examiner—Jill A. Johnston
Attorney, Agent, or Firm—Fay, Sharpe, Beall, Fagan, Minnich & McKee

[57] ABSTRACT

The body portion (A) of a small portable sterilizer has a face panel (46) against which a door (B) is selectively closed. The face panel defines an access opening for a sterilization chamber (10) which receives a cassette (C), an access opening for an anti-microbial concentrate chamber (20) which receives a powdered or other sterilant concentrate, and an outlet opening (50) from a microbe filter which filters microbes from incoming rinse water. The face plate and the door define fluid flow channels (48, 52) therebetween for selectively directing sterilant solutions and rinse solutions among the antimicrobial concentrate chamber, the sterilization chamber, and the microbial filter. The cassette is configured to assure that it is inserted into the sterilization chamber with a unique orientation such that its fluid inlet apertures (114) and outlet apertures (124) are at preselected locations. The door includes generally U-shaped projections (116) which abut an outer surface of the cassette in the sterilization chamber partially surrounding the fluid inlet apertures. The U-shaped projections assure that the cassette is seated in the sterilization chamber and provide a well which directs the circulating fluids into the cassette inlet apertures. A pair of gaskets (56, 86) surround the active portion of the face panel. A vacuum pump (90) selectively draws a vacuum in an annular region (88) between the gaskets, which vacuum locks the door against the face plate in a sealed, closed position. To assure a fluid tight seal, the gaskets are O-rings which are pressed by the vacuum into V-shaped grooves (82, 84).

21 Claims, 7 Drawing Sheets

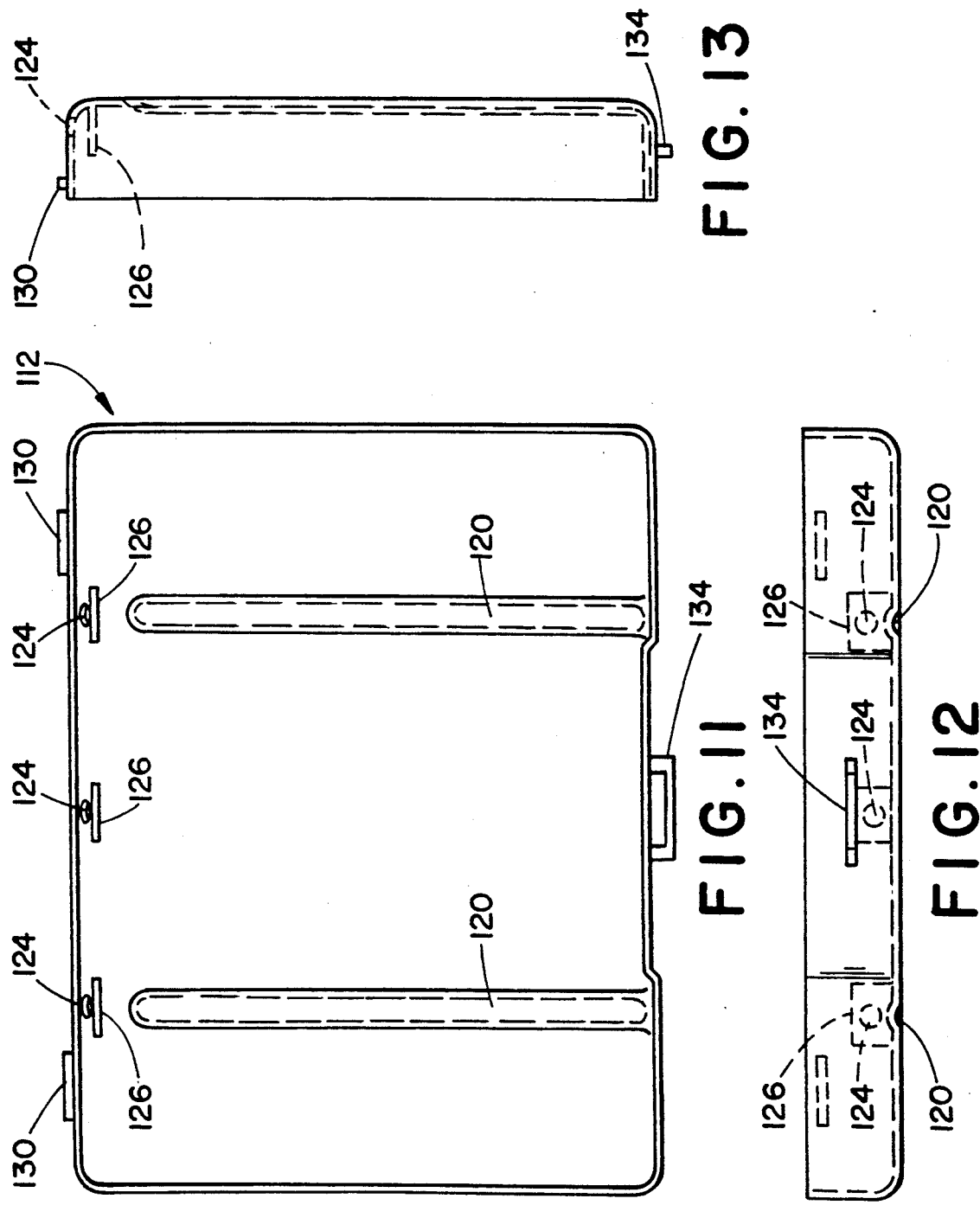

OFFICE SIZE INSTRUMENT STERILIZATION SYSTEM

This application is a continuation-in-part of U.S. application Ser. No. 07/349,304 filed May 9, 1989, now U.S. Pat. No. 5,091,343 which, in turn, is a continuation-in-part of U.S. application Ser. No. 07/140,388, filed Jan. 4, 1988, now U.S. Pat. No. 4,892,706 which, in turn, is a continuation-in-part of U.S. application Ser. No. 06/826,730, filed Jul. 6, 1986, now U.S. Pat. No. 4,731,222. This application is also a continuation-in-part of U.S. application Ser. No. 07/342,189, filed Apr. 24, 1989, now U.S. Pat. No. 5,116,575 which, in turn, is a continuation-in-part of U.S. application Ser. No. 07/229,917, filed Aug. 8, 1988, now U.S. Pat. No. 5,077,008 which, in turn, is a continuation-in-part of U.S. application Ser. No. 07/165,189, filed Mar. 17, 1988, now U.S. Pat. No. 5,037,623 and also a continuation in part of U.S. application Ser. No. 07/140,388, filed Jan. 4, 1988, now U.S. Pat. No. 4,892,706, which are also continuations-in-part of U.S. application Ser. No. 06/826,730, filed Jul. 6, 1986, now U.S. Pat. No. 4,731,222.

BACKGROUND OF THE INVENTION

The present invention pertains to the decontamination art. It finds particular application in conjunction with sterilizing medical equipment and will be described with particular reference thereto. It will be appreciated, however, that the invention is also applicable to disinfecting systems as well as to microbially decontaminating a wide range of items, including medical and dental instruments, laboratory equipment, industrial equipment, and the like.

Disinfection connotes the absence of pathogenic life forms. Sterilization connotes the absence of all life forms, pathogenic or not. Often, sterilization is measured against the elimination of bacterial endospores which are the living organisms most resistant to conventional sterilants. Microbial decontamination is used herein as the term generic to both sterilization and disinfection.

Many hospitals and larger facilities have a central sterilizing area. Medical equipment to be sterilized is forwarded to the sterilizing area where it is processed by trained technicians and returned to the individual medical units. One problem with a central sterilizing area is that the turnaround time on sterilization is relatively long, often on the order of days. This long turnaround time increases the need for duplicate sets of medical equipment, sufficient numbers of sets that a sterilized set is available for each patient during the turnaround time. Another drawback of the central sterilization area resides in the complexity of transporting and sorting equipment, the storage areas required, and the space required for a central sterilization facility. Like medical instruments tend to be interchanged such that physicians who send well cared for equipment for sterilization often receive mistreated equipment in return. A result and perhaps greater problem is that equipment is not always sent to a central sterilization facility before it is reused.

Commonly, medical equipment is sterilized in a steam autoclave. Autoclaves kill like forms with a combination of high temperature and pressure. Steam autoclaves have several drawbacks. The high temperature pressure vessel tends to be relatively bulky and heavy. The high temperature and pressure tends to dry or curtail the useful life of endoscopes, rubber and plastic device, lenses and other portions of devices made of polymeric materials, and the like. Further, the sterilizing cycle is relatively long from the start of the cycle until the instruments are cool enough to use.

More sensitive medical equipment is often sterilized with an ethylene oxide gas system which is thermally less severe than steam. However, the ethylene oxide has several drawbacks. First, the instruments must be exposed to the ethylene oxide for a relatively long time, on the order of 3½ hours. Thereafter, an 8-12 hour degassing period is normally required for removing absorbed ethylene oxide from plastic and other ethylene oxide absorptive materials. The pressure and depressurization cycles of ethylene oxide sterilization may damage lens and other delicate instruments. Second, the ethylene oxide is relatively expensive. Third, ethylene oxide is sufficiently toxic and volatile that extensive precautions and training are commonly taken to assure operator safety. Usually, a trained operator and a dedicated facility are required.

Liquid sterilization systems are often used for heat-sensitive and other delicate instruments. Commonly, a technician mixes a liquid sterilant composition and manually immerses the items until he deems them sterilized. The high degree of manual labor introduces numerous uncontrolled and unreported variables into the sterilization process. Manual timing of the immersion raises assurance problems that the item was immersed for a sufficient duration. Further, sterilants tend to weaken, i.e. have a limited shelf life. Variations in the duration between when the technician mixed the sterilant and actually used it also raises problems with sterilization assurance and reproduceability of the microbial decontamination.

Another problem with the prior art liquid system resides in the corrosive nature of the strong oxidants that are commonly used as liquid sterilants. Normally, the sterilized items are rinsed to remove chemical residues. This rinsing also adds a variable that reduces the assurance the item has been disinfected or sterilized. Once rinsed, the item is susceptible to reinfection by airborne microbes.

In accordance with the present invention, a new and improved sterilization apparatus and method are provided which overcome the above-referenced problems and others.

SUMMARY OF THE INVENTION

In accordance with one aspect of the present invention, a distributant sterilization system is provided. A relatively small, compact sterilization unit is provided for one or a small number of medical service provider areas, such as examination rooms.

In accordance with a more specific aspect of the present invention, a microbial decontamination system is provided. A body portion has a face panel which defines an access opening to a microbial decontamination chamber, an access opening to an anti-microbial concentrate receiving chamber, and a rinse fluid outlet opening in direct fluid communication with a filter means for removing at least pathogenic organisms from incoming rinse fluid. A door closes over and seals to at least a portion of the face panel surrounding the microbial decontamination chamber access opening, the anti-microbial concentrate chamber access opening and the rinse fluid outlet opening. A means defines fluid flow paths between the face panel and an interior surface of the door. The flow paths provide fluid communication among the microbial decontamination chamber access opening, the anti-microbial concentrate chamber access opening and the rinse fluid outlet opening. A fluid circulating means selectively circulates fluid through the anti-microbial concentrate chamber to form an anti-microbial solution. The anti-microbial solution flows through the fluid flow paths to the microbial decontamination chamber and through the microbial decontamination chamber. The circulating means selectively supplies the fluid through the filter means to create a microbially decontaminated rinse fluid that flows out of the rinse fluid outlet opening, through the flow paths to the microbial decontamination chamber to rinse the anti-microbial solution from items in the microbial decontamination chamber.

In accordance with another aspect of the present invention, two gaskets are provided between the face panel and the interior surface of the door. The two gaskets surround the microbial decontamination chamber access opening, the anti-microbial concentrate chamber access opening, and the rinse fluid outlet opening, and interconnecting flow paths. The two gaskets define a generally annular region therebetween. A vacuum means selectively draws a vacuum in the annular region to force the door and face panel into a tight fluid sealing relationship.

In accordance with another more limited aspect of the present invention, a cassette for receiving items to be microbially decontaminated is received in the microbial decontamination chamber. The cassette includes upper and lower portions which mate in a fluid tight sealed relationship. The upper and lower portions are openable to provide access to the interior for inserting items to microbially decontaminated or for withdrawing microbially decontaminated items for use. Fluid inlet apertures are defined in an uppermost portion of the cassette when inserted in the microbial decontamination chamber for enabling the cassette to receive and be filled with anti-microbial solution and the rinse fluids. At least one fluid outlet aperture is defined in a lowermost portion of the cassette when inserted in the microbial decontamination chamber to enable the interior of the cassette to be drained of the anti-microbial solution and the rinse fluids. A means is provided for preventing airborne microbial contaminants from passing through the fluid inlet and outlet apertures. A means is provided for controlling the orientation with which the cassette is received in the microbial decontamination chamber such that the fluid inlet apertures are at the uppermost portion of the cassette and the fluid outlet apertures are at the lowermost portion of the cassette.

One advantage of the present invention is that it assures sterilization or disinfection of medical and other items with liquid sterilants.

Another advantage of the present invention is that it is relatively compact and easy to use. Medical personnel, such as doctors, dentists, and nurses, can sterilize their own instruments on site without a specialized technician.

Another advantage of the present invention is that it makes sterilized equipment readily available. Not only is equipment sterilized quickly on site, it is held in an organized microbial contamination-free inventory ready for use.

Still further advantages of the present invention will become apparent to those of ordinary skill in the art upon reading and understanding the following detailed description.

BRIEF DESCRIPTION OF THE DRAWINGS

The present invention may take form in various parts and arrangements of parts, or in various steps and arrangements of steps. The drawings are only for purposes of illustrating a preferred embodiment and are not to be construed as limiting the invention.

FIG. 11 is a bottom view of the cassette of FIG. 2;

FIG. 12 is a front view of the cassette of FIG. 11; and,

FIG. 13 is a side view of the cassette of FIG. 11.

DETAILED DESCRIPTION OF THE PREFERRED EMBODIMENT

With reference to FIGS. 1, 2, 3, and 4, a sterilizing apparatus A is configured to sit on a countertop or other convenient work surface. Preferably, the sterilizing apparatus is dimensioned such that it fits on a standard 60 cm (24 inch) deep countertop without interfering with overhead cupboards. A front door B is manually openable to provide access for inserting a cartridge C and a sterilant, preferably in the form of a cup or ampule D, into the system.

Figure 1:
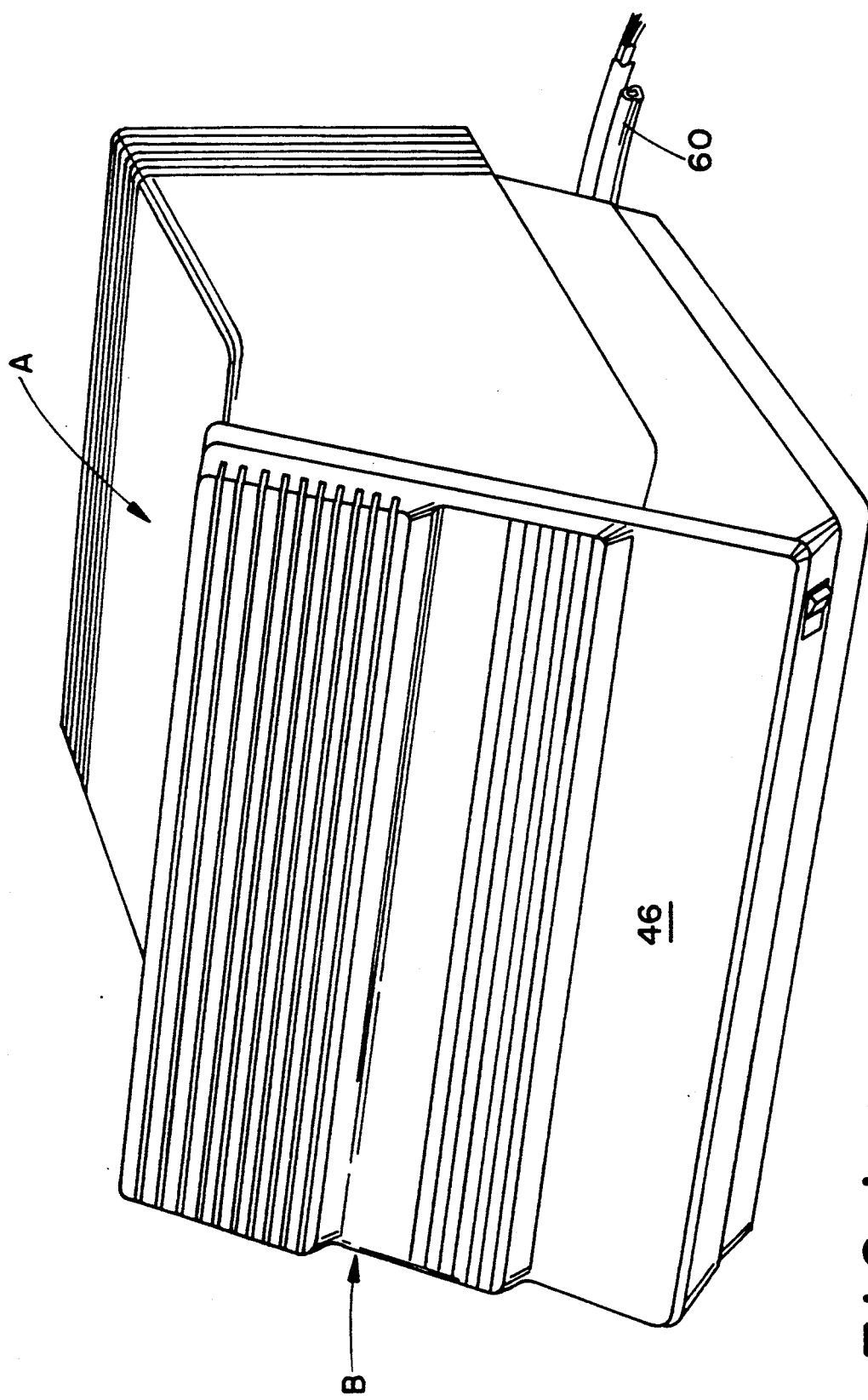
FIG. 1 is a perspective view of a microbial decontamination system in accordance with the present invention.
Figure 2:
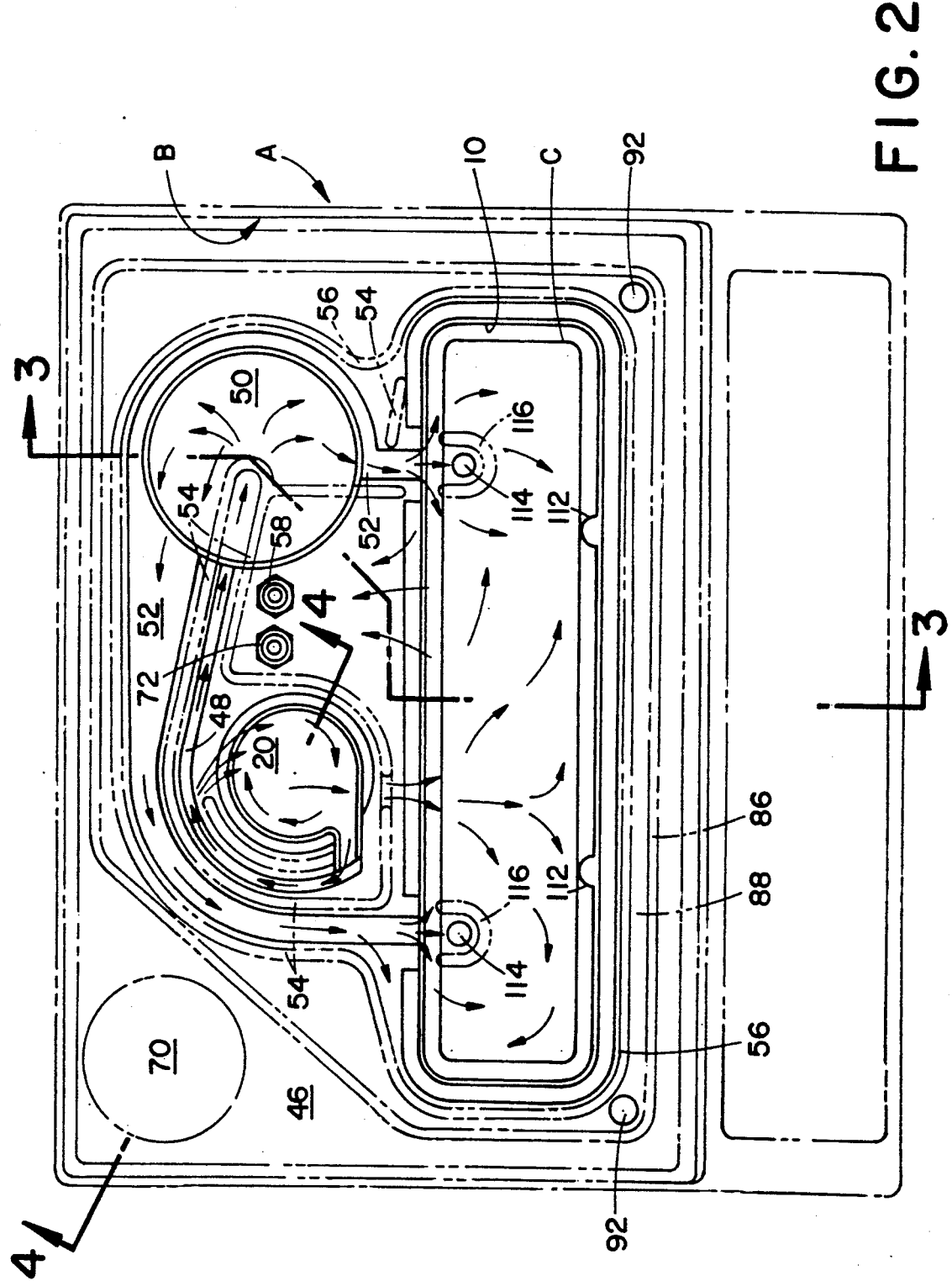
FIG. 2 is a front view of the system of FIG. 1 with the front door shown in phantom and with a cartridge of items to be sterilized.
Figure 3:
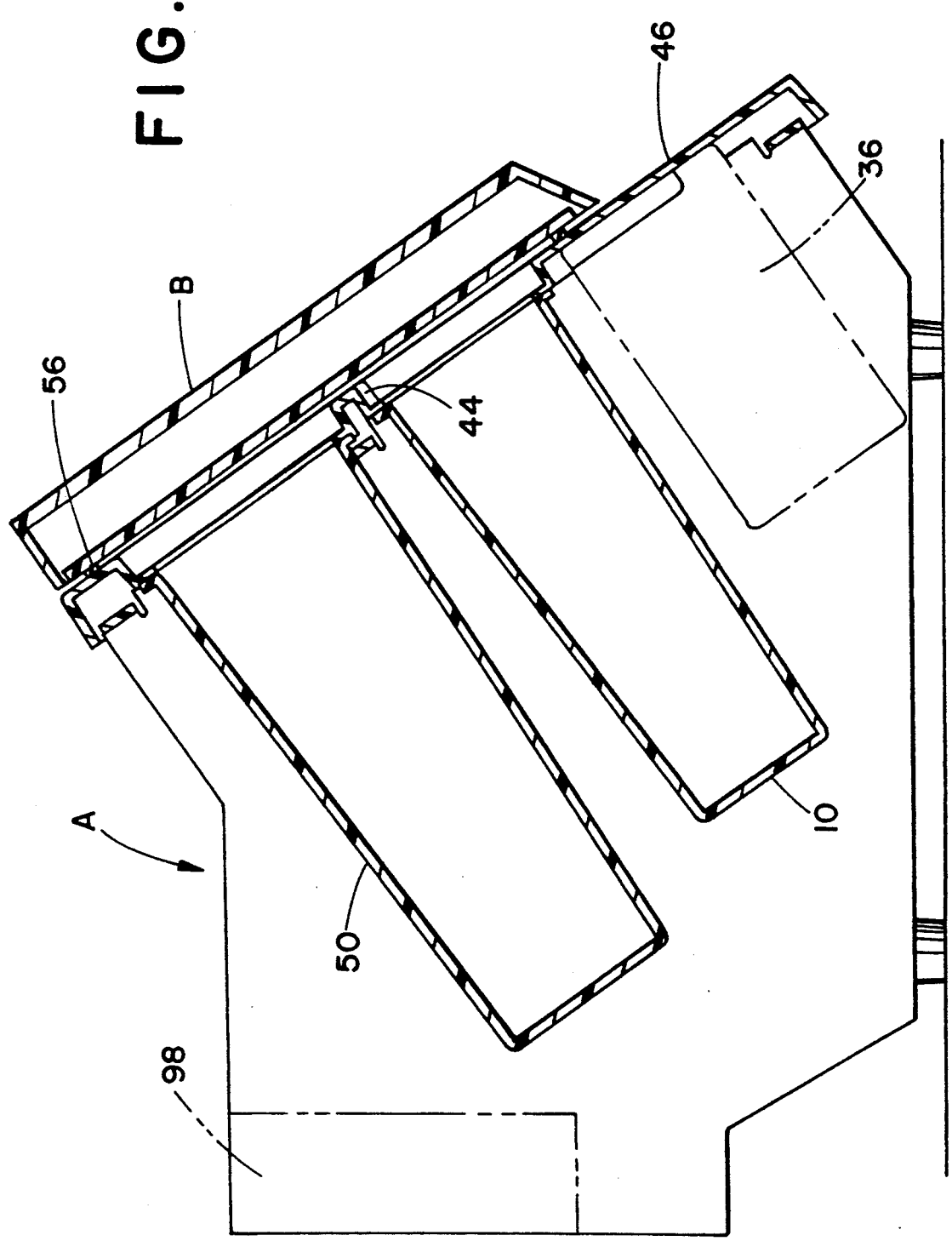
FIG. 3 is a sectional view through section 3—3 of FIG. 2.
Figure 5:
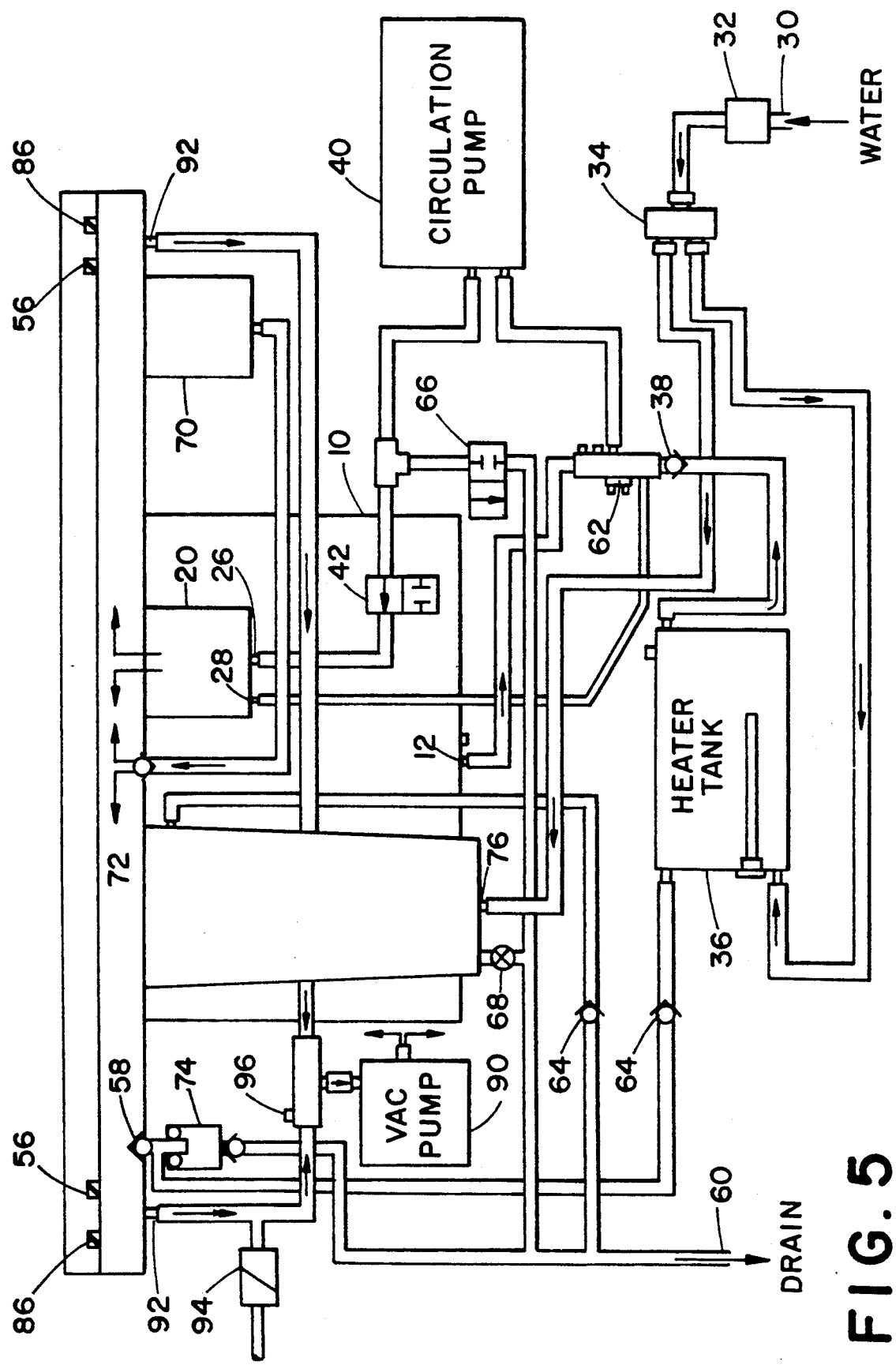
FIG. 5 is a diagrammatic illustration of the plumbing system of the system of FIG. 1.
Figure 10:
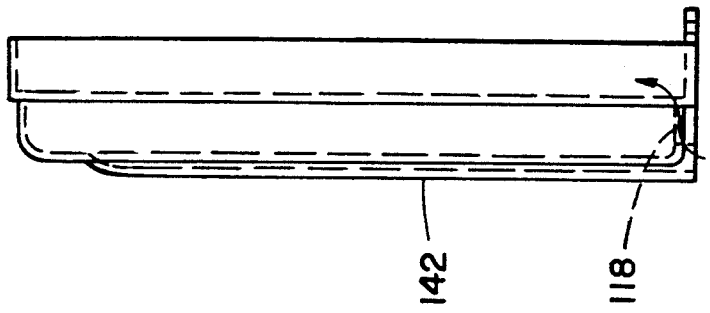
FIG. 10 is a side view of the top portion of the cassette of FIG. 8.
Figure 8:
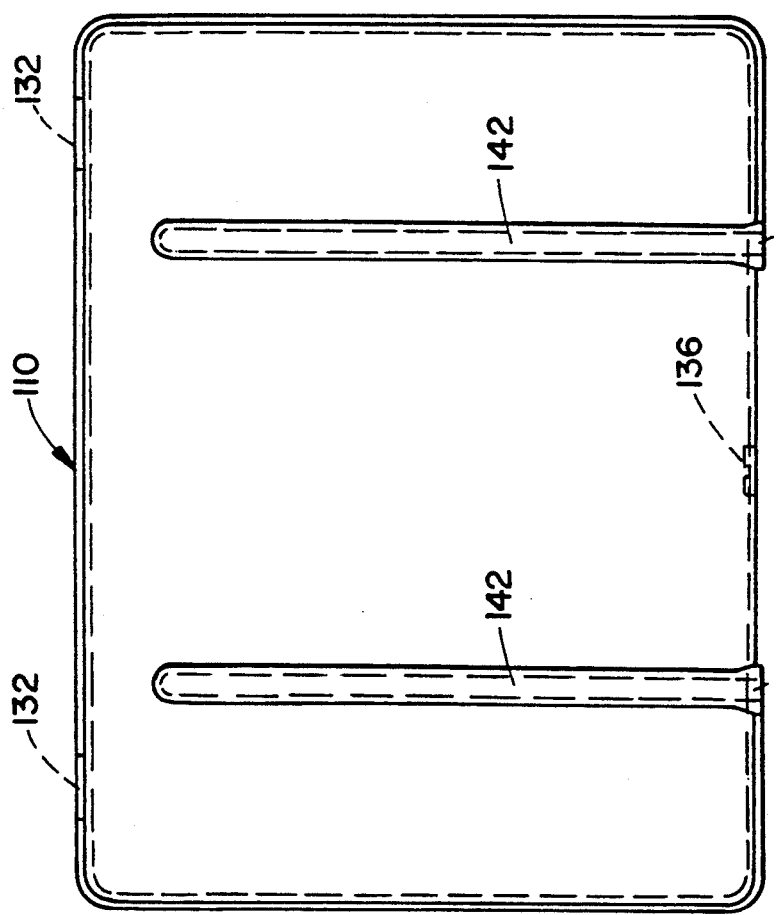
FIG. 8 is a top view of the cassette of FIG. 2.
Figure 9:
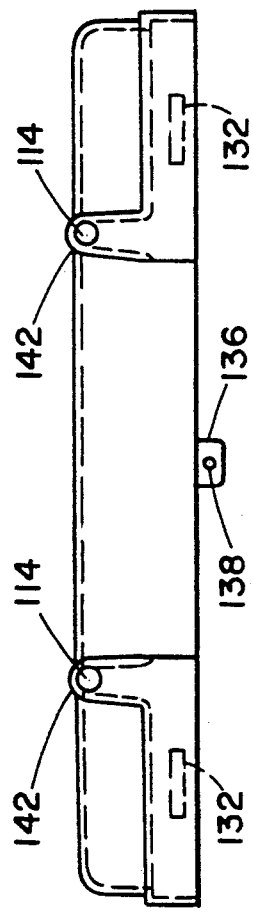
FIG. 9 is a front view of a top portion of the cassette of FIG. 8.

With continuing reference to FIGS. 2 and 3, and further reference to FIG. 5, items to be sterilized are loaded in the cartridge C which is slidably received in a cartridge receiving chamber 10. The chamber 10 is open at the front to receive a free flow of sterilant through the front. A drain or outlet port 12 at the end enables sterilant to circulate continuously over and through the cartridge.

Figure 4:
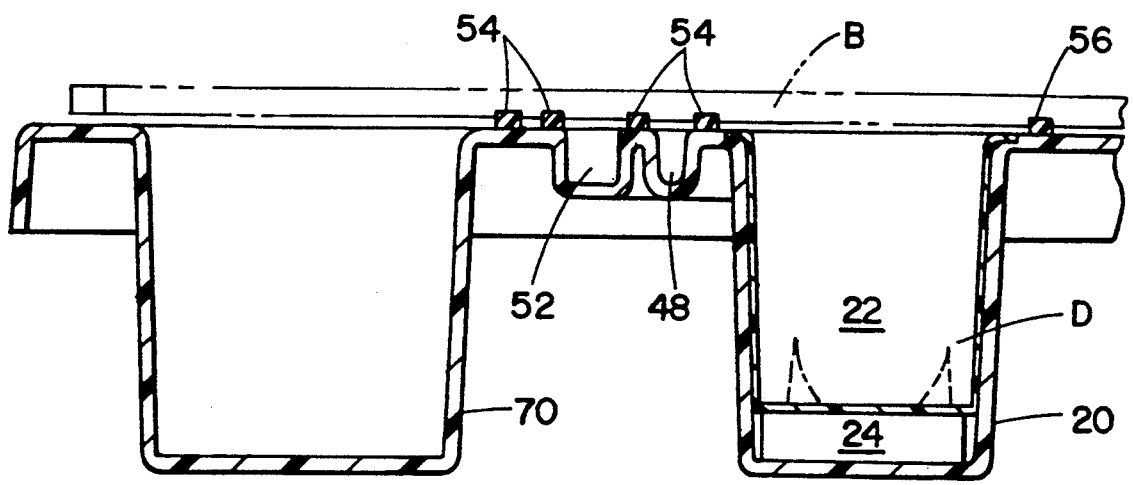
FIG. 4 is a sectional view through section 4—4 of FIG. 2.

With reference to FIGS. 2, 4, and 5, an anti-microbial composition is loaded into an anti-microbial mixing chamber 20. A premeasured dose of the anti-microbial agent, in the illustrated embodiment, is held in a cup 22 which is pierced by a cutter 24 as it is inserted into the mixing chamber 20. The anti-microbial cup is again open at the front to allow free fluid flow therefrom. An inlet port 26 receives water or other fluids with which the anti-microbial agent is diluted or dissolved. An anti-microbial mixing chamber drain port 28 provides an outlet for the water sterilant mixture to assist in recirculation.

Various anti-microbial agents may utilized. In the preferred embodiment, the anti-microbial agent is a mixture of powders which reacts when wet to form a sterilant, such as a strong oxidant, corrosion inhibitors, and a wetting agent. More specifically to the preferred embodiment, the dry ingredients include a water-soluble acid precursor and a water-soluble persalt which, when dissolved in water, form a peracetic acid solution with an anti-microbially effective concentration of peracetic acid. The dry ingredients further include a buffer, e.g. a borate, for bringing the pH to a neutral level to inhibit steel corrosion. The dry ingredients include other corrosion inhibitors, such as a molybdate for inhibiting aluminum and steel corrosion, a triazole for inhibiting copper and brass corrosion, and the like. Powdered wetting and sequestering agents may also be included. In the preferred embodiment, the acid precursor is acetylsalicylic acid and the persalt is sodium perborate. The total volume of dry ingredients is such that the resultant water solution has a concentration of peracetic acid of at least 0.2% W/V—a biocidally effective concentration.

Other oxidizing or anti-microbial agents can also be generated in situ, such a chlorine dioxide, chlorine, hydrogen peroxide, and mixtures thereof. For example, the powdered ingredients may include a mixture of potassium chromates, sodium chloride, and phosphates. As another example, hydrogen peroxide can be generated from a mixture of sodium borate and phosphates. Chlorine dioxide can be generated from a mixture of sodium chlorate and lithium chlorite. Sodium chloride can be added to peracetic acid to produce hyperchlorous acid.

Other copper and brass corrosion inhibitors are also contemplated, such as benzotriazoles, tolytriazoles, mercaptobenzathiozol, azoles, benzoates, and other five-membered ring compounds. Other anti-corrosives include chromates, dichromates, tungstates, vanidates, borates, and combinations thereof. A suitable sequestering agent for sequestering any precipitated calcium and magnesium salts is sodium hexametaphosphate.

Of course, liquid sterilants, such as liquid hydrogen peroxide, peracetic acid, and the like may also be utilized. If liquids are utilized, it is preferred that the liquid be held in a cup or vial from which the liquid may be aspirated by water flowing through the sterilant cup. The cup or vial may also be punctured or fractured on insertion to permit a free-flowing communication between the water and the liquid sterilant.

With particular reference to FIG. 5 and continuing reference to FIGS. 1–4, a water inlet 30 is connected by flexible hose with a sink or other source of water. A pressure regulator 32 regulates the pressure to a preselected pressure. An inlet valve 34 is selectively actuated to channel fill water to a heater tank 36. The heater tank maintains the water therein, preferably about 5 liters, at a preselected elevated temperature. As cold water enters the heater tank, it forces hot water in front of it through a check valve 38. The check valve 38 separates a sterile side of the system and a non-sterile portion of the system adjacent the heater tank.

A circulation pump 40 circulates the hot water through a control valve 42 to the anti-microbial mixing chamber 20. The water mixes and interacts with the sterilant composition to form a liquid sterilant that flows out the open front end of the mixing chamber 20.

With particular reference to FIG. 2, water flowing out of the front of the mixing chamber flows through channels 44 defined between a face plate 46 and the door B. The face plate 46 is a molded structure which defines the mixing chamber 20, the cassette chamber 10, the flow paths 44, and other elements of the system. A channel 48 extends between the mixing chamber and a water sterilizing filter 50. The face plate also defines a passage 52 extending from the sterilizing filter 50 to the cassette receiving reservoir 10. Gaskets 54 on the door assist in defining and sealing the flow paths 48 and 52 and permit fluid feedback to increase mixing turbulence around the mixing chamber 20. A peripheral gasket 56 between the door and the face plate defines the periphery of fluid flow paths defined between the face and the door.

The circulation pump 40 pumps hot water from the heater tank 36 through the mixing chamber 20 displacing all air from the sterilization chamber 10 and substantially all air between the face plate 46 and the door B and replacing the air with the sterilant or anti-microbial solution. At the highest point, an overflow valve 58 permits excess sterilant solution to be discharged to a drain 60. The cassette receiving chamber outlet port 12 is also connected through a supplemental heater 62 with the circulation pump 40 such that the sterilant solution is actively drawn through the sterilization chamber 10, heated, and recirculated.

The circulation pump continues to recirculate the sterilant solution through the cassette receiving chamber 10 and the various plumbing paths until the inside of the cassette and all items re sterilized, the outside of the cassette is sterilized, the exterior surface of the face panel inside the gaskets, the interior surface of the door inside the gaskets, all accessible surfaces of the sterile water filter 50, the interior surfaces of all tubing, fittings, and valve surfaces through which fluid is circulated, and the circulation pump are sterilized or disinfected. Once all these surfaces are microbially decontaminated, the anti-microbial solution is drained through the drain outlet 60 into the drain of a sink or other liquid waste disposal system. Because strong oxidants, such as peracetic acid, breakdown relatively quickly to water, salt, and oxygen, there is no pollution or polluting contaminants that require special disposal. The drain outlet 60 is connected by check valves 64 and controlled valves 66 and 68 with various drain points of the system. To assure substantially complete drainage, the control valve 66 is opened and control valve 42 is closed such that the circulation pump withdraws the anti-microbial solution from the system and pumps it through controlled drain valve 66 to the drain outlet 60. The plumbing is preferably physically positioned for complete drainage through outlet valve 66 by gravity.

A microbially decontaminated, preferably sterile, air filter 70 is connected between exterior air and a check valve 72. The filter is a porous membrane whose apertures are sufficiently small that microbes are not permitted to pass. In this manner, sterile air is allowed to fill the volume left as the anti-microbial solution is drained. A float type air vent 74 permits air to be vented to the drain 60 but seals if its chamber fills with liquid to prevent liquid to flow therethrough back into the sterilization chamber 10.

After the sterilant is drained, the drain control valve 66 is returned to its closed state and the recirculation control valve 42 is returned to its open state. Water inlet valve 34 also channels incoming water to an inlet port 76 of the now sterilized, microbe removing water filter 50. The water filter 50 is again a porous membrane whose apertures are sufficiently small that water is passed but microbes, particularly all pathogenic microbes, are restrained. The surfaces of the membrane toward the open end have all been sterilized by the liquid sterilant as have most underlying portions. As the incoming water passes through the membrane, sterile rinse water passes through the front outlet end of the sterile water filter and flows through channel 52 toward the front opening of the cassette chamber 10. When rinse water is introduced such that sterile rinse water fills the entire volume between the face and the door insert, the circulation pump circulates the fluid to assure that sterilant residue is removed from all interior surfaces. Once at least the items in the cassette C have been fully rinsed, the controlled valves 42 and 66 change states such that the rinse solution is pumped out of the system and replaced with sterile air. It will be noted that all surfaces with which the sterile rinse comes in contact including the plumbing and valve surfaces engaged during circulation were previously sterilized or microbially decontaminated during the sterilization or microbial decontamination portion of the cycle.

Figure 6:
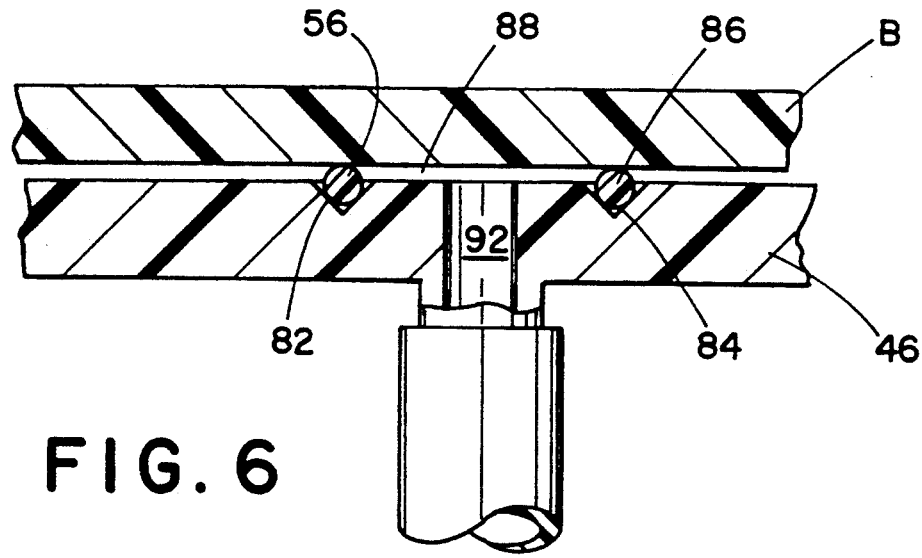
FIG. 6 is a sectional view illustrating details of an O-ring sealing arrangment between the door and gaskets of the system of FIG. 1.

With the particular reference to FIG. 6 and continuing reference to FIGS. 2, 3, and 4, a fluid tight seal between the lid and the body portion is maintained by a pneumatic pressure system 80. A pair of 90° V-shaped grooves or seats 82, 84 are defined in one or both of the face portion 46 and the lid B. O-ring seals 56, 86 are mounted partially in the V-shaped grooves and partially extending outward therefrom. The V-shaped grooves and O-rings define two closed loop paths around the fluid circulation portion and define a path 88 therebetween. A vacuum pump 90 is connected by appropriate tubing with vacuum ports 92 in the area between the two seals. The vacuum pump maintains a preselected negative pressure which causes the lid and body portions to squeeze the O-ring into the seats with a fluid tight seal. A vacuum release valve 94 is selectively actuated to release the vacuum to allow the lid to be opened. Optionally, a water sensor 96 is mounted along the vacuum tubing to sense a failure of the sealing arrangment which results in anti-microbial or rinse fluid being sucked past the inner gasket 56 into the vacuum path 88. An electronics module 98 includes a microprocessor which is programmed to operate the valves, pumps, and other elements in the sequence described above. Preferably, the electronics include a clock and date module, temperature sensors, a key pad, and a printer for printing a record of the time, date, operator, and system operating parameters.

Figure 7:
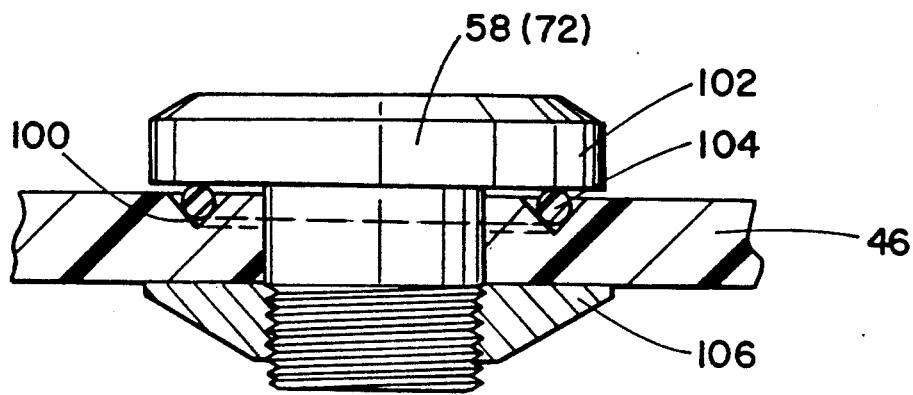
FIG. 7 is a view in partial section illustrating details of an O-ring sealing arrangement between the check valves and face panel of the system of FIG. 1.

As illustrated in FIG. 7, a similar arrangement is used to seal check valves 58 and 72 to the face 46. The face 46 defines a V-shaped groove 100 with a 90° angle surrounding the check valve. The check valve has a flange 102 over and closely adjacent to the face overhanging the groove 100. An O-ring 104 is received in the V-shaped groove abutting the underside of the flange 102. A threaded nut or flange member 106 engages threads on the exterior of the check valve to urge the check valve flange to press the O-ring into the groove in a fluid tight seal.

With reference to FIGS. 2, and 8-13, the cassettes C each include a top portion 110 which matingly connects with a bottom portion 112. The bottom portion may include a tray or rack (not shown) which has appropriate catches, compartments, guides, and the like for holding the instruments or items to be sterilized in a neat and organized pattern. For example, the tray may be configured to hold and organize a set of dental examination instruments in an appropriate arrangement to facilitate dental use. The exact design of the tray, of course, will vary with the requirements of each end user.

The top 110 of the cassette includes ports 114 at an uppermost portion to receive anti-microbial and rinse solutions and permit the escape of any air which might be trapped in the cassette. The ports 114 are disposed to be in alignment with flow paths 52. The lid has U-shaped gasket portions 116 which engage the periphery of the cassette around the lower portion of ports 114 to direct the liquids from flow paths 52 into the cassette. The cassette receiving chamber is canted to horizontal such that the ports 114 are at the highest point of the cassette. Baffles 118 present a tortuous path between the ports 114 and the interior of the cassette. By and large, biological contaminants will not follow a tortuous path to gain access into an otherwise sealed enclosure. A tortuous path has been found reliable in preserving sterility of the enclosed items.

The cassette bottom 112 includes channels 120 which receive or interact with guide ridges 122 in the sterilization chamber 10 to assure right-way-up receipt. Optionally, other means might be provided for assuring that the cassette C is inserted with the cartridge bottom down and the cartridge top up. The cassette bottom also includes apertures 124 in a lowermost portion of a rear wall. The low placement of the apertures assures complete drainage of sterilant and rinse solutions from the cassette. Baffles 126 present a tortuous path to prevent biological contamination of items in the cassette after sterilization or disinfecting.

The cassette bottom portion includes projections 130 from a rear vertical wall which are received in slots 132 in the top portion rear wall to assure that the top and bottom portions remain interconnected. The lower portion also includes a U-shaped bale 134 on a forward wall through which a tab 136 depending from the upper portion forward wall is slidably received. The tab and bale, particularly aperture 138 in the tab for receiving a sealing element. More specifically, once the sterilization process is completed, a frangible seal is placed through the tab aperture and the bale and sealed such that it must be broken in order to open the container. Preferably, the seal is encoded with an identification number that identifies the sterilization cycle. This number may be utilized to cross-reference a more detailed listing of sterilization parameters, such as the date of sterilization, the operator, a serial number of the sterilant concentrate, water temperature, sterilization time, and other parameters which verify the sterilization. Alternately, the seal may carry a larger portion or all of such sterilization assurance information.

The top portion has a peripheral flange 140 with a slight outward bevel which tightly and frictionally engages the outer peripheral vertical surface of the bottom portion to provide a tight friction seal therebetween.

Preferably, the top portion 110 has projections or ribs 142 that are positioned at the same distances apart and from the edges as the channels 120 on the bottom portion such that if the cartridge is inverted, the cassette channels and ribs would be reversed. The sterilization chamber 10 tapers to be wider at the front and narrower at the back. The cassette is of approximately the same height as the sterilization chamber at the rear. The upward rids 142 on the top portion terminate before the rear of the cassette or are tapered toward the rear to provide minimal clearance. If the cassette is inverted and inserted upside down, the interaction of the ribs 142 and guide ridges 122 lift the wall of the chamber 10 before it is fully inserted. In this manner, insertion of the cassette in the sterilization chamber 10 upside down is prevented. Of course, other means may be provided for preventing the cartridge from being inserted upside down.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A microbial decontamination system comprising:
   a horizontally extending decontamination chamber;
   an anti-microbial concentrate receiving chamber in which a received anti-microbial concentrate is mixed with a fluid to form an anti-microbial solution;
   a rinse means for providing a pathogenic organism free rinse solution;
   a body portion having a face panel which defines:
      a first access opening for providing horizontally sliding access to the microbial decontamination chamber,
      a second access opening to the anti-microbial concentrate receiving chamber,
      a rinse fluid outlet opening in direct fluid communication with the rinse means for introducing the pathogenic organism free rinse fluid;
   a door which closes over and seals to at least a portion of the face panel which includes the first access opening, the second access opening, and the rinse fluid outlet opening, an interior surface of the door and the face panel defining a fluid passage therebetween when the door is in a closed, sealed position relative to the face panel;
   a means for defining fluid flow channels in the fluid passage between the face panel and the interior surface of the door, the fluid flow channels providing fluid communication among the first access opening, the second access opening, and the rinse fluid outlet opening;
   a fluid circulating means for selectively circulating fluid through the anti-microbial concentrate chamber to form the anti-microbial solution, circulating the anti-microbial solution flowing through the fluid flow channels to the microbial decontamination chamber and through the microbial decontamination chamber, and for selectively supplying the rinse fluid from the rinse means to the rinse fluid outlet opening and through the fluid flow channels to the microbial decontamination chamber to rinse the anti-microbial solution from items in the microbial decontamination chamber.

2. The microbial decontamination system as set forth in claim 1 further including a cassette for holding items to be microbially decontaminated, the cassette having fluid access means which enables the anti-microbial solution and the rinse fluid to flow into the cassette, the cassette and the first access opening being dimensioned such that the cassette is horizontally slidable into the microbial decontamination chamber.

3. A microbial decontamination system comprising:
   a microbial decontamination chamber within which items are selectively decontaminated;
   an anti-microbial concentrate receiving chamber for receiving an anti-microbial concentrate;
   a rinse means for providing a pathogenic organism free rinse fluid;
   a body portion having a face panel which defines:
      a first access opening to the microbial decontamination chamber,
      a second access opening to the anti-microbial concentrate receiving chamber,
      a rinse fluid outlet opening in direct fluid communication with the rinse means for selectively introducing the pathogenic organism free rinse fluid;
   a door which closes over and seals to at least a portion of the face panel which includes the first access opening, the second access opening, and the rinse fluid outlet opening;
   a means for defining fluid flow paths between the face panel and an interior surface of the door when the door is in a closed, sealed position relative to the face panel, the fluid flow paths providing fluid communication among the first access opening, the second access opening, and the rinse fluid outlet opening;
   a fluid circulating means for selectively circulating fluid through the anti-microbial concentrate chamber to form an anti-microbial solution, for selectively circulating the anti-microbial solution through the fluid flow path means to the microbial decontamination chamber, and for selectively supplying the rinse fluid through the rinse fluid outlet opening through the flow path means to the decontamination chamber;
   two gasket means which surround the first access opening, the second access opening, the rinse fluid outlet opening, and the flow path means and which two gasket means provide a sealed generally annular region therebetween; and
   a vacuum means for selectively drawing a vacuum in the annular region between the gasket means for selectively locking the door into sealing engagement with the face panel.

4. The system as set forth in claim 3 wherein the gasket means includes O-rings and further including V-shaped grooves in at least one of the door and the face panel in which the O-rings are partially received.

5. A microbial decontamination system comprising:
   a microbial decontamination chamber within which items are selectively decontaminated;
   an anti-microbial concentrate receiving chamber for receiving an anti-microbial concentrate;
   a water inlet for receiving water from an external water source;
   an inlet valve means for selectively controlling the flow of water from the water inlet;
   a heater tank for heating water received from the inlet valve means;
   a rinse water filter means for filtering at least pathogenic organisms from received water to form a pathogenic organism free rinse fluid;
   a body portion having a face panel which defines:
      a first access opening to the microbial decontamination chamber,
      a second access opening to the anti-microbial concentrate receiving chamber, a rinse fluid outlet opening in direct fluid communication with the rise means for selectively introducing the pathogenic organism free rinse fluid;

a door which closes over and seals to at least a portion of the face panel which includes the first access opening, the second access opening, and the rinse fluid outlet opening;

a means for defining fluid flow paths between the face panel and an interior surface of the door when the door is in a closed, sealed position relative to the face panel, the fluid flow paths providing fluid communication among the first access opening, the second access opening, and the rinse fluid outlet opening;

a circulation pump means for pumping heated water from the heater tank to at least the anti-microbial concentrate chamber;

a drain means for selectively draining fluid from the microbial decontamination chamber, the rinse decontamination means, and the flow paths between the face panel and the door;

a fluid connector means for connecting the inlet valve means, the heater tank, the circulation pump, the anti-microbial concentrate chamber, the decontamination chamber, the rinse decontamination means, and the drain means;

a microbe removing air filter means operatively connected with the flow paths between the face panel and the door for filtering microbial contaminants from air and which allows the microbially decontaminated air to replace the anti-microbial solution and the rinse fluid as each is drained.

6. The system as set forth in claim 5 further including:

a check valve means having an inlet and extending through the face panel and connected with one of the drain means and the microbe removing air filter means, the check valve having a flange adjacent the face panel;

the face panel defining a V-shaped groove around the check valve inlet end;

an O-ring disposed in the V-shaped groove around the O-ring; and a means for urging the check valve and face plate together forcing the O-ring into the V-shaped groove forming a fluid tight seal between the face plate and the O-ring flange.

7. A microbial decontamination system comprising:

a microbial decontamination chamber within which items are selectively decontaminated;

an anti-microbial concentrate receiving chamber for receiving an anti-microbial concentrate;

a rinse means for supplying pathogenic organism free rinse fluid;

a body portion having a face panel which defines:

a first access opening to the microbial decontamination chamber, a second access opening to the anti-microbial concentrate receiving chamber, a rinse fluid outlet opening in direct fluid communication with the rinse means for selectively introducing the pathogenic organism free rinse fluid;

a door which closes over the seals to at least a portion of the face panel which includes the first access opening, the second access opening, and the rinse fluid outlet opening;

a means for defining fluid flow paths between the face panel and an interior surface of the door when the door is in a closed, sealed position relative to the face panel, the fluid flow paths providing fluid communication among the first access opening, the second access opening, and the rinse fluid outlet opening;

a cassette for receiving items to be microbially decontaminated, the cassette including:

upper and lower portions which mate together in a sealed relationship, such that the upper and lower portions are openable to provide access to the interior for inserting or withdrawing items to be microbially decontaminated, the upper and lower portions being dimensioned for sliding receipt in the microbial decontamination chamber;

a plurality of fluid access apertures defined in the cassette for enabling the cassette when inserted in the microbial decontamination chamber to be filled with the anti-microbial solution and the rinse fluid and drained;

a fluid passing means for preventing airborne microbial contaminants from passing through the fluid access apertures to items in an interior of the cassette when the cassette is removed from the microbial decontamination chamber;

a means for controlling an orientation with which the cassette is inserted into the microbial decontamination chamber, whereby the cassette is prevented from being inserted upside down;

a fluid circulating means for selectively circulating fluid through the anti-microbial concentrate chamber to form an anti-microbial solution, circulating the anti-microbial solution flowing through the fluid flow paths to the microbial decontamination chamber and through the microbial decontamination chamber and cassette, and circulating the microbially decontaminated rinse fluid flows through the flow paths to the microbial decontamination chamber and the cassette to rinse the anti-microbial solution from items in the cassette.

8. The system as set forth in claim 7 wherein the cassette further includes a tab and bale arrangement operatively connected with the upper and lower cassette portions for receiving a frangible seal which must be broken to open the cassette, whereby a frangible seal is attachable to provide assurance that the cassette has remained closed and the items therein have maintained their microbially decontaminated condition.

9. The system as set forth in claim 7 wherein at least one of the fluid access apertures of the cassette is adjacent an uppermost corner of the upper portion, which uppermost access aperture is disposed closely adjacent the door when the cassette is inserted in the microbial decontamination chamber and wherein the flow paths direct the anti-microbial solution and the rinse fluids to the uppermost aperture.

10. The system as set forth in claim 9 wherein the flow paths are defined in the face panel and further including a generally U-shaped projection from an interior surface of the door, which U-shaped projection abuts a surface of the cassette and partially surrounds the uppermost aperture, the U-shaped projection being aligned with the flow path when the door is closed such that the U-shaped projection defines a well which directs fluids into the uppermost aperture.

11. A microbial decontamination system comprising:

a body portion in which a decontamination chamber and an anti-microbial concentrate receiving chamber are housed;

a substantially vertical face panel which defines a first access opening to the microbial decontamination chamber and a second access opening to the anti-microbial concentrate receiving chamber;

a door means which closes over and seals at least a portion of the face panel which includes the first and second access openings, the door and the face panel defining fluid flow paths therebetween;

a locking means for selectively locking the door means and face panel together in a fluid tight sealing relationship;

a cassette for receiving items to be microbially decontaminated, the cassette being configured for horizontal sliding receipt into the first access opening and the decontamination chamber;

a fluid circulating means for selectively circulating a fluid to the anti-microbial concentrate receiving chamber to form an anti-microbial solution and for selectively circulating the anti-microbial solution and a microbially decontaminated rinse solution through the microbial decontamination chamber and the received cassette for selectively microbially decontaminating and rinsing item received in the cassette.

12. A microbial decontamination system comprising:
a microbial decontamination chamber for receiving items to be microbially decontaminated;
an anti-microbial concentrate receiving chamber for receiving an anti-microbial concentrate;
a body within which the microbial decontamination chamber and the anti-microbial concentrate receiving chamber are housed, the body having a face area through which a microbial decontamination chamber access opening in communication with the microbial decontamination chamber and an anti-microbial concentrate chamber access opening in communication with the anti-microbial concentrate chamber are defined;
a door means which closes over at least a portion of the face area which includes the microbial decontamination chamber access opening and the anti-microbial concentrate chamber access opening, the door means and the face area defining a fluid flow passage therebetween which provides fluid communication between the microbial decontamination chamber and the anti-microbial concentrate chamber;
a fluid circulating means for circulating fluid through the anti-microbial chamber to form an anti-microbial solution, through the fluid passage between the door means and the face area, and through the microbial decontamination chamber;
a cassette which is slidably receivable in the microbial decontamination chamber, the cassette having at least a fluid inlet opening adjacent an uppermost corner disposed in alignment with the fluid flow channels of the face area for receiving anti-microbial solution flow therefrom and having at least one fluid outlet opening at a lowermost portion thereof, the cassette further including a means for preventing airborne microbial contaminants from passing through the fluid inlet and outlet openings to prevent items in an interior of the cassette from being reached from such airborne microbial contaminants.

13. The system as set forth in claim 12 further including generally U-shaped projection portions from an interior surface of the door, which U-shaped projection portions abut a surface of the cassette and partially surround the fluid inlet opening, the U-shaped projection portions being aligned with the fluid flow channels when the door is closed such that the U-shaped projection portions define a well which directs fluids into the fluid inlet opening.

14. The system as set forth in claim 12 wherein the cassette including upper and lower cassette portions which are frictionally received in a fluid tight sealing relationship, a tab and bale arrangement being operatively connected with the upper and lower cassette portions for receiving a frangible seal which must be broken to open the cassette.

15. A microbial decontamination system comprising:
a body portion which includes a generally vertical face panel and which defines a generally horizontally extending microbial decontamination chamber, the face panel defining a decontamination chamber access opening through which a cassette is horizontally slidable into the decontamination chamber which cassette holds items to be microbially decontaminated, the cassette including:
upper and lower cassette portions which mate together in a fluid tight relationship such that the upper and lower portions are openable to provide access to the interior for inserting items to be microbially decontaminated or for withdrawing microbially decontaminated items,
at least one fluid inlet opening disposed adjacent an uppermost portion of the cassette disposed in the microbial decontamination chamber for receiving an anti-microbial solution and a rinse fluid,
at least one fluid outlet opening defined in a lowermost portion of the lower portion for enabling the cassette to be drained of the anti-microbial solution and the rinse fluid,
a means for preventing airborne microbial contaminants from passing through the fluid inlet and outlet openings to microbially contaminate items in an interior of the cassette when the cassette is removed from the decontamination chamber,
means for controlling an orientation with which the cassette is inserted into the microbial decontamination chamber;
a generally vertically oriented door means which seals against the face panel to close the microbial decontamination chamber;
a fluid circulating means for circulating the anti-microbial solution and the rinse fluid at least through the cassette fluid inlet opening and the fluid outlet opening to microbially decontaminate items in the cassette.

16. The system as set forth in claim 15 wherein the face panel further defines an anti-microbial concentrate receiving chamber and a chamber for receiving a rinse water filter means for removing at least pathogenic organisms for incoming water and wherein a plurality of paths are defined between the face panel and the door means for circulating water and anti-microbial solution among the anti-microbial concentrate receiving chamber, microbial decontamination chamber, and the water filter chamber.

17. The system as set forth in claim 16 further including a generally U-shaped projection from an interior surface of the door means, which U-shaped projection abuts the surface of the cassette and partially surrounds the fluid inlet opening, the U-shaped projection being aligned with the flow path such that the U-shaped projection defines a well which directs fluid into the cassette fluid inlet opening.

18. The system as set forth in claim 17 further including a means for selectively locking the door means into sealing engagement with the face panel.

19. A microbial decontamination system comprising:
a body portion in which a microbial decontamination chamber and an anti-microbial concentrate receiving chamber are defined;
a generally vertical face panel that defines a first access opening to the microbial decontamination chamber and a second access opening to the anti-microbial concentrate receiving chamber;
a generally vertically oriented door which closes over and seals peripherally around at least a portion of the face panel which includes the first and second access openings, a vertical fluid passage is being defined between the face panel and the door to provide fluid communication among at least the first and second access openings;
a fluid circulating means for selectively circulating fluid through the anti-microbial concentrative receiving chamber to form an anti-microbial solution, the anti-microbial solution flowing between the door and face panel and through the microbial decontamination chamber; and,
a cassette for holding items to be microbially decontaminated, the cassette having fluid access means which enables the anti-microbial solution and rinse fluid to flow into the cassette, the cassette being dimensioned to be received with the horizontal sliding motion through the first access opening in the microbial decontamination chamber.

20. The microbial decontamination system as set forth in claim 19 further including projections defined means when the door means is closed to define fluid flow channels that providing fluid communication among the first access opening, the second access opening, and a rinse fluid inlet opening.

21. The microbial decontamination system as set forth in claim 20 wherein the projections include at least one generally U-shaped projection projecting from an interior surface of the door adjacent an anti-microbial solution receiving aperture of the cassette, the U-shaped projection being aligned with an anti-microbial solution flow channel such that the U-shaped projection defines a well which directs fluids into the cassette aperture.

* * * * *